US012183456B2

(12) United States Patent
Kumar

(10) Patent No.: US 12,183,456 B2
(45) Date of Patent: Dec. 31, 2024

(54) RECYCLING COMPONENTS IN MEDICAL DEVICES

(71) Applicant: MatrixCare, Inc., Bloomington, MN (US)

(72) Inventor: Sunjit Kumar, Bihar (IN)

(73) Assignee: MATRIXCARE, INC., Bloomington, MN (US)

( * ) Notice: Subject to any disclaimer, the term of this patent is extended or adjusted under 35 U.S.C. 154(b) by 326 days.

(21) Appl. No.: 17/655,917

(22) Filed: Mar. 22, 2022

(65) Prior Publication Data

US 2023/0307117 A1    Sep. 28, 2023

(51) Int. Cl.
*G16H 40/40* (2018.01)
*G06Q 10/30* (2023.01)

(52) U.S. Cl.
CPC ............ *G16H 40/40* (2018.01); *G06Q 10/30* (2013.01)

(58) Field of Classification Search
None
See application file for complete search history.

(56) References Cited

U.S. PATENT DOCUMENTS

| | | | | | |
|---|---|---|---|---|---|
| 5,965,858 | A * | 10/1999 | Suzuki | ............... | G06Q 10/0875 705/29 |
| 6,308,089 | B1 * | 10/2001 | von der Ruhr | .... | A61B 5/14542 600/338 |
| 2008/0312978 | A1 * | 12/2008 | Binney | ................ | G06Q 10/087 705/28 |
| 2012/0143211 | A1 * | 6/2012 | Kishi | ..................... | A61B 34/37 606/130 |
| 2012/0252403 | A1 * | 10/2012 | Becerra | .................. | G06Q 10/10 455/405 |
| 2014/0200580 | A1 * | 7/2014 | Joseph | ...................... | A61L 2/00 422/26 |
| 2017/0068792 | A1 * | 3/2017 | Reiner | ............... | A61B 17/1214 |
| 2017/0215963 | A1 * | 8/2017 | Tang | ...................... | A61B 90/08 |
| 2017/0284860 | A1 * | 10/2017 | Dickerson | ............... | A61B 5/00 |
| 2019/0107815 | A1 * | 4/2019 | Miller | .............. | G06Q 10/06315 |

* cited by examiner

*Primary Examiner* — John A Pauls
(74) *Attorney, Agent, or Firm* — Patterson + Sheridan, LLP

(57) ABSTRACT

Embodiments herein describe tracking the use of medical devices to update their remaining life. In addition to tracking the remaining life of the overall device, the embodiments herein can track the remaining life of each component which may be greater than the life of the medical device. Unlike typical modular devices which are replaced after they break or exceed their expected life, one-time use (or limited use) medical devices may be limited to use by a specific patient before they are discarded. The embodiments herein can use communication between healthcare providers and a tracker database to track the usage of a medical device and update the remaining life of its components to identify components that can be recycled after the medical device is no longer being used.

20 Claims, 9 Drawing Sheets

| Device Entry 125 → | | | |
|---|---|---|---|
| Medical Device A (ID) — 205  Device Lifetime  Device Usage — 215 | Recyclable 405 | Sterilization Required 410 | Remaining Life — 130 |
| Face Apparatus (ID) — 210A  Component Lifetime  Component Usage — 220A | Y | Y | Remaining Life — 140A |
| Electric Motor (ID) — 210B  Component Lifetime  Component Usage — 220B | Y | N | Remaining Life — 140B |
| Ventilator (ID) — 210C  Component Lifetime  Component Usage — 220C | Y | Y | Remaining Life — 140C |
| Oxygen Supply (ID) — 210D  Component Lifetime  Component Usage — 220D | Y | N | Remaining Life — 140D |
| Filter (ID) — 210E  Component Lifetime  Component Usage — 220E | N | N/A | Remaining Life — 140E |

Component Entry 135A, 135B, 135C, 135D, 135E

FIG. 4

RECYCLING COMPONENTS IN MEDICAL DEVICES

BACKGROUND

Field

Embodiments of the present disclosure relate to tracking patient usage of medical devices to build new medical devices from recycled components.

Description of the Related Art

Many medical devices are limited to single use, or a limited number of uses before they must be discarded. For example, a medical device used by one patient may be discarded after a single use, or the medical device can be used several times by the same patient, but cannot be used by a different patient.

SUMMARY

One embodiment herein is a method that includes registering a one-time use medical device in a database where a device entry in the database for the medical device includes at least one component entry for a recyclable component in the medical device; tracking a usage of the medical device by a patient; updating a remaining life of the recyclable component based on the usage of the medical device; upon determining the patient is finished with the medical device, determining whether the recyclable component has sufficient remaining life to be recycled based on a threshold; upon determining the recyclable component has sufficient remaining life, removing the recyclable component from the medical device; and transporting the recyclable component to be placed in a new medical device.

Another embodiment herein is a non-transitory computer readable medium comprising instructions to be executed in a processor, the instructions when executed in the processor perform an operation. The operation includes registering a one-time use medical device in a database where a device entry in the database for the medical device includes at least one component entry for a recyclable component in the medical device; tracking a usage of the medical device by a patient; updating a remaining life of the recyclable component based on the usage of the medical device; upon determining the patient is finished with the medical device, determining whether the recyclable component has sufficient remaining life to be recycled based on a threshold; upon determining the recyclable component has sufficient remaining life, outputting instructions to remove the recyclable component from the medical device; and outputting instructions to transport the recyclable component to be placed in a new medical device.

Another embodiment herein is a system that includes a processor and memory storing code which, when executed by the processor, performs an operation. The operation includes registering a one-time use medical device in a database where a device entry in the database for the medical device includes at least one component entry for a recyclable component in the medical device; tracking a usage of the medical device by a patient; updating a remaining life of the recyclable component based on the usage of the medical device; upon determining the patient is finished with the medical device, determining whether the recyclable component has sufficient remaining life to be recycled based on a threshold; upon determining the recyclable component has sufficient remaining life, outputting instructions to remove the recyclable component from the medical device; and outputting instructions to transport the recyclable component to be placed in a new medical device.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

FIG. 4 illustrates an entry in a database for a medical device, according to one embodiment.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1:
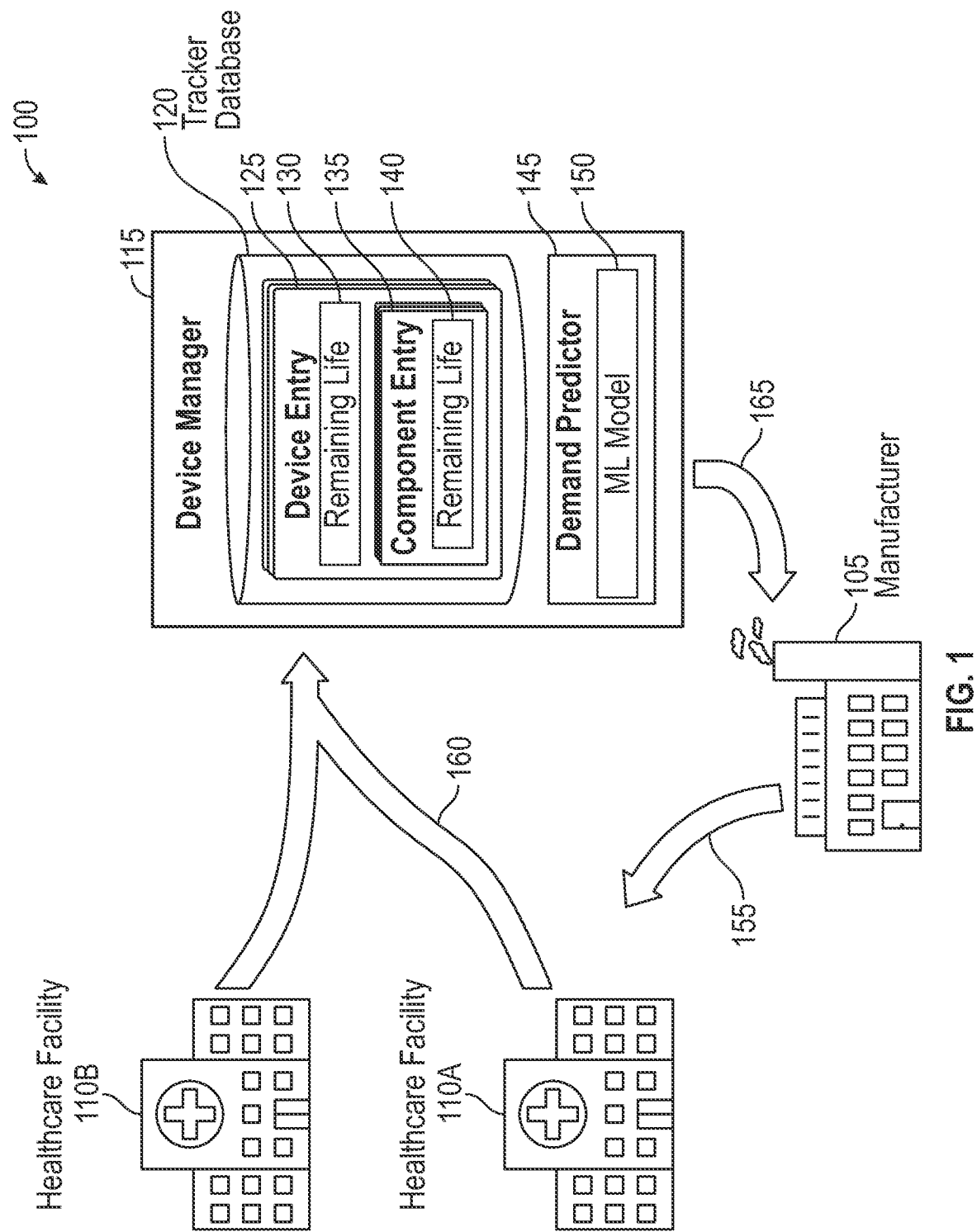
FIG. 1 illustrates a block diagram of tracking patient usage of a medical device to identify recyclable components, according to one embodiment.

Embodiments herein describe tracking the usage of medical devices to update their remaining life. In addition to tracking the remaining life of the overall device, the embodiments herein can track the remaining life of each component which may be greater than the life of the medical device. Unlike in typical modular devices which are replaced after they break or exceed their expected life, one-time use (or limited use) medical devices may be limited to use by a specific patient before they are discarded for multiple reasons such as cross contamination or government regulations. For example, an insurance provider may require only new medical devices be given to its members. This can be wasteful and expensive considering old medical devices may be discarded when many of its components still have much of their expected life remaining.

Recycling medical devices, or recycling components in medical devices, is a technical problem that has not previously been solved. The embodiments herein rely on communication between healthcare providers and a tracker database to track the usage of a medical device and update the remaining life of its components. For example, the healthcare providers can inform the tracker database when a medical device has been assigned to a patient (or put in use) and the length of time the patient used the device. For instance, the patient may use the device intermittently during her stay at a healthcare facility. With this information, the tracker database can update the remaining life of the components.

Unlike prior systems where a modular device is flagged for recycling after it breaks or has met its expected life, here the medical device may be recycled after a patient (or a limited number of patients) have stopped using the device (e.g., when the patient is discharged from the facility or has recovered from the condition requiring the use of the medical device). As mentioned above, this often occurs when there is substantial life remaining for the modular components in the device. The tracker database can then be referenced to identify components with remaining life and these components can be removed from the current device and recycled into a new medical device.

Because of sanitation concerns, some components may be sterilized before being recycled while others do not. For example, a breathing apparatus may include a ventilator and a face mask that are sanitized before being recycled but may include an electric motor or an oxygen supply that are not. The sanitization process for each component can be used to adjust its remaining life. For example, a one-time use breathing apparatus may contain a ventilator with six months of remaining life. However, after consider the cost or wear-and-tear that the sanitization process incurs, the remaining life of the ventilator may be reduced to zero, which disqualifies it from being recycled. However, because the electric motor does not require sanitization, its remaining life is unaffected. In this manner, any sanitization requirements can be reflected in the remaining life of the components.

In one embodiment, machine learning can be used to predict the amount of medical devices that will be available for recycling at a future date. Given the amount of medical devices that a healthcare provider may have, it may be difficult to predict in the future how many of these devices will be ready for recycling. A machine learning (ML) model can be trained to evaluate each patient currently assigned a specific type of medical device (e.g., a breathing apparatus, special bed, pump, etc.) and predict when that patient will no longer need the device. The ML model can then do this for each medical device to provide a prediction of the number of single-use medical devices that will be available in the future. The system can then estimate how many new medical devices can be formed from recyclable components in these medical devices. This number can then be compared to a predicted forecast of the total number of medical devices the healthcare provider will need to then determine how many new medical devices should be ordered from a manufacture (which do not contain any recycled components). For example, assume the ML model predicts that in one month the healthcare provider will have twenty breathing apparatus that are no longer needed, which can then be used to build ten new breathing apparatuses from the recycled components. The demand forecast may predict the healthcare provider will need thirty total new breathing apparatus in a month. Thus, the healthcare provider knows it needs to order twenty new breathing apparatus from the manufacture in order to satisfy the total demand. In this manner, machine learning can be used to predict, at a future date, how many new medical devices can be built using recycled components.

FIG. 1 illustrates a block diagram of tracking patient usage of a medical device to identify recyclable components, according to one embodiment. FIG. 1 illustrates a system 100 that includes healthcare facilities 110 which can represent hospitals, outpatient clinics, long-term care facilities, surgery centers, and the like. These healthcare facilities 110 can be owned and operated by the same healthcare provider or by different healthcare providers.

The system 100 also includes a manufacture 105 which builds and distributes to the healthcare facilities medical devices as shown by the arrow 155. That is, the manufacture 105 may sell the medical devices to the healthcare provider or providers operating the healthcare facilities 110. In one embodiment, the medical devices are one-time use (or single use) medical devices. For example, due to sanitation concerns, some medical devices may be limited to one patient before they are typically discarded. In another example, some private or government payors (e.g., insurance providers) may require a patient to use only a new type of medical device, such as some special beds. Thus, once the patient is done with the bed, it is discarded. This leads to significant waste and expense.

However, the same prohibitions or concerns may not apply to new medical devices that are built or assembled using recycled components from one-time use (or limited use) medical devices. For example, a new breathing apparatus can be assembled using parts from an old breathing apparatus that never came into contact with the patient, such as an electric motor. Or the components can be put through a sanitization process before being assembled into a new medical device. Thus, new medical devices can be built using some, or all, of the recycled components from old medical devices.

One-time use medical devices are especially suitable for identifying components that can be recycled given that a patient may be done with the device well before the device has reached its end of life. Further, even if the device as a whole has reached its end of life, the components in the device may have a longer life. Thus, the embodiments herein describe techniques for recycling medical devices, such as one-time use medical devices with modular components, or devices which may often be discarded before the end of life of the device or its components. This is unlike typical modular devices which are only recycled after an end of life or when the device breaks or malfunctions.

To identify recyclable components, the healthcare facilities 110 communicate with a device manager 115 as shown by arrow 160. The device manager 115 (e.g., a software application or system) includes a tracker database 120 and a demand predictor 145. The tracker database 120 is not limited to any particular type of database so long as it can perform the functions described herein. As shown, the tracker database 120 stores multiple devices entries 125 that each correspond to a medical device used by the healthcare facilities 110. For example, when receiving a new medical device from the manufacturer 105, the healthcare facilities (or a healthcare provider) can register the medical device with the device manager 115 which in turn adds a new device entry 125 for that device into the tracker database 120.

In this example, each device entry 125 includes the remaining life 130 of medical device as well as includes component entries 135 for one or more components in the medical device. For example, the device entry 125 may include a component entry (also referred to as a sub-entry) for each modular or replaceable component in the medical device. The device entries 125 store the remaining life 140 of each of the components. The remaining lives 130, 140 may be reduced based on receiving updates from the healthcare facilities 110. For example, the facilities 110 may inform the device manager 115 when the medical device corresponding to the device entry 125 is put in service (e.g., used by a patient) and how long the device was used. The device manager 115 can then update the remaining life 130 for the device and the remaining lives 140 of the components to reflect the use by the patient. For example, assume the medical device and the components in the device have the same life expectancy. As the device is used, the remaining lives 130, 140 would decrease by the same amount, and have the same values. However, if the medical device and a component did not have the same life expectancy (e.g., the medical device has a life expectancy of one year but an electric motor in the device has a life expectancy of two years), then if the patient used the device for six months, the remaining life 130 of the device is six months but the remaining life 130 of the electric motor is 1.5 years. Thus, the device manager 115 can use the tracker database 120 to track the remaining life 130 of the device as a whole using the device entry 125 as well the remaining lives 140 of the individual components in the device using the component entries 135.

In addition to providing updates regarding the use of the medical devices, the healthcare facilities 110 can inform the device manager 115 when a medical device is being discarded or is no longer in service. For one-time use medical devices, this can occur when the patient no longer needs the device. However, instead of simply discarding the medical device, the device manager 115 can decide whether to recycle one or more of the components in the device. For example, the device manager 115 may recycle any component that has remaining life 140 (e.g., remaining life that has not been reduced to zero due to patient use). Or the device manager 115 may recycle any component that has remaining life 140 that meets or exceeds the expected life of the medical device. For example, if a new medical device has an expected life of 1 year, and a component in an old medical device has a component with a remaining life 140 of 1 year or more, that component can be recycled and used in a new medical device. The different criteria for determining when a component has sufficient remaining life to be recycled is discussed in more detail in FIG. 3 below.

The device manager 115 also includes a demand predictor 145 which predicts a number of new medical devices that can be assembled from recycled components from old medical devices purchased by the healthcare facilities 110. In one embodiment, the device manager 115 can evaluate the currently available recyclable components from old medical devices (as determined by the device manager 115) and determine how many new medical devices can be assembled using the recyclable components. These new medical devices can include a mix of recycled components as well as new components. For example, a new medical device can include some recycled components as well as brand new components.

The demand predictor 145 also includes a ML model 150 for predicting a number of old medical devices that will be discarded (e.g., flagged for recycling) by the healthcare facilities 110 at a future date or further time frame (e.g., in the next month). The ML model 150 can be trained to predict how long each patient currently assigned a medical device will use it. With this information, the ML model 150 can indicate how many medical devices (and the components therein) will be available for recycling. With this, the device manager 115 can determine how many new medical devices can be built using the components in those devices. The device manager 115 can then determine how many new medical devices should be ordered from the manufacture 105 as shown by arrow 165. That is, the demand predictor 145 can use the ML model 150 to predict how many recyclable components will be available at a future time and then use this information to determine how many new medical devices can be built from those components, which can reduce the number of new medical devices that are ordered from the manufacturer 105 to satisfy the demand. This is discussed in more detail in FIGS. 6 and 7. The ML model 150 can be implemented using a neural network, such as a convolution neural network or a recurrent neural network.

In general, one-time use medical devices can include devices that are used only one time or are used multiple times by the same patient. A one-time use medical device may be used by the same patient over a non-continuous time frame. For example, the patient may use the device one day, but not the next day, but does use the device the following day. In one embodiment, the patient uses the medical device until her condition that required the medical device is resolved. In any case, one-time use medical devices may be discarded while some or all of the components of the device (as well as the device itself) have remaining life.

While FIG. 1 illustrates tracking the use of medical devices at the healthcare facilities 110, the embodiments herein can also be applied to medical devices used by patients in their homes. For example, a healthcare provider may provide a medical device to the patient. The patient may then return the medical device to the healthcare provider who then informs the device manager 115. In turn, the device manager 115 can use the amount of time the patient used the medical device to calculate the remaining life 130 of the device as well as the remaining lives 140 of the components in the device. The device manager 115 can then determine whether to recycle the components to build a new medical device.

Figure 2:
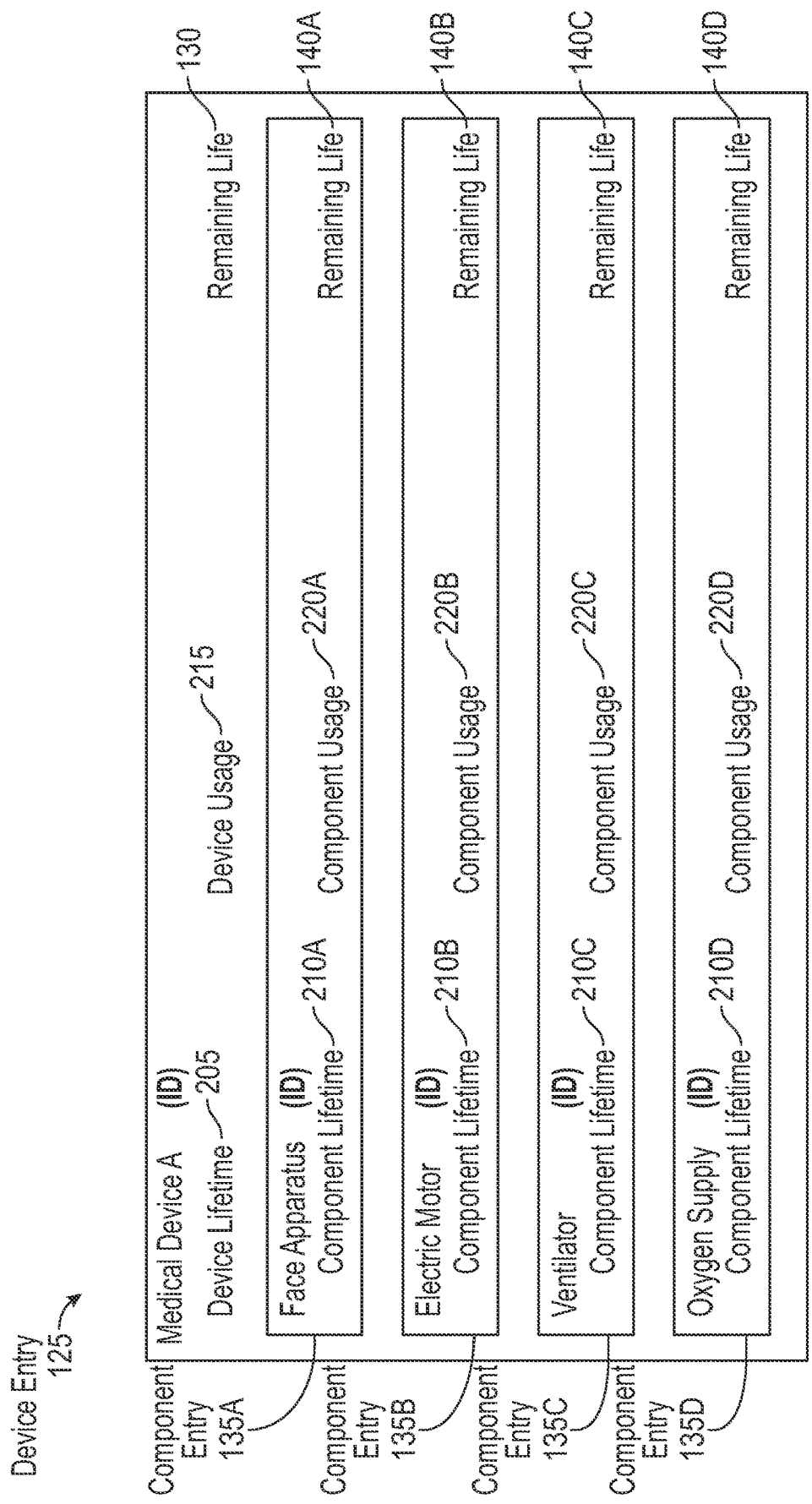
FIG. 2 illustrates an entry in a database for a medical device, according to one embodiment.

FIG. 2 illustrates a device entry 125 in the tracker database 120 in FIG. 1, according to one embodiment. The top of the entry 125 indicates this entry is for Medical Device A. The entry 125 can store an ID of the device, which can be a unique ID such as a serial number. The healthcare facilities can use the ID to update the device entry 125 such as informing the database that the medical device has been assigned to a patient, how long the medical device was used by the patient, or that the medical device is ready to be recycled (or discarded).

The entry 125 also includes a device lifetime 205 which indicates the expected life of the medical device. The entry 125 also includes a device usage 215 which indicates the amount of time the medical device has been in use (which can be by one patient if it is a one-time use medical device or by multiple patient if it is a multi-use medical device). The device manager can use the device lifetime 205 and the device usage 215 to calculate the remaining life 130 of Medical Device A. For example, the manufacture may state the desired or design lifetime of Medical Device A is one year, which is stored as the device lifetime 205 in the entry 125. If the healthcare facility informs the device manager that Medical Device A has been in use for two months, then the device manage can update the remaining life 130 to ten months. In this manner, the device manager can track the remaining life 130 as the device as a whole. Thus, as the healthcare provider continues to send updates to the device manager regarding the usage of Medical Device A, if the remaining life 130 ever reaches zero, then the device manager can inform the healthcare provider who then may choose to discard the device.

The device entry 125 also includes component entries 135A-D (i.e., sub-entries) for components in Medical Device A. The entry 125 can include component entries 135 for every component in the device, or may maintain entries only for components that can be recycled, such as modular components that can easily be removed and added to a new medical device. In this example, the component entry 135A corresponds to a face apparatus of Medical Device A, the component entry 135B corresponds to an electric motor in Medical Device A, the component entry 135C corresponds to a ventilator in Medical Device A, and the component entry 135D corresponds to an oxygen supply in Medical Device A. The component entries 135A-D can include an ID for each component, which can be a unique ID such as a serial number. The IDs may be assigned by the manufacture of the components, or could be assigned by the device manager.

Each component entry 135 includes a component lifetime 210 indicated the expected or desired lifetime of the corresponding component. The component lifetimes 210A-D of the components will likely be different from each other, and may be set by the respective manufactures of the components. For example, the face apparatus may have a four month lifetime 210A while the electric motor has a two year lifetime 210B. In one embodiment, the device lifetime 205 of Medical Device A may equal the shortest component lifetime 210. That is, the device lifetime 205 is only as long as the component with the shortest lifetime 210.

The component entries 135 also include a component usage 220 (e.g., a component usage time) indicating the amount of time the particular component has been used by a patient. If Medical Device A is a brand new device without any recycled components, then the component usages 220 for the components (as well as the device usage 215) will be the same. However, if one of the components is a recycled component from a medical device that has been recycled, then its usage 220 would be longer than components that are brand new.

In one embodiment, the device manager can subtract the component usage 220 from the component lifetime 210 to identify the remaining life 140 for each component. While FIG. 2 illustrates using the component lifetime 210 and the component usage 220 to determine the remaining life 140, other factors can also be considered. For example, the device manager may weigh the component usage 220 differently for the components. For instance, the electric motor may wear out faster if used in humid environments, in which case the component usage 220B may be weighted so that its remaining lifetime 140B is decreased faster than the remaining lifetime of other components.

In one embodiment, the device entry 125 may be deleted when the healthcare facility or provider confirms Medical Device A is being discarded. At that time, the device manager can determine whether to recycle one or more of the components to be used to build one or more new medical devices. This process is discussed in more detail below.

Figure 3:
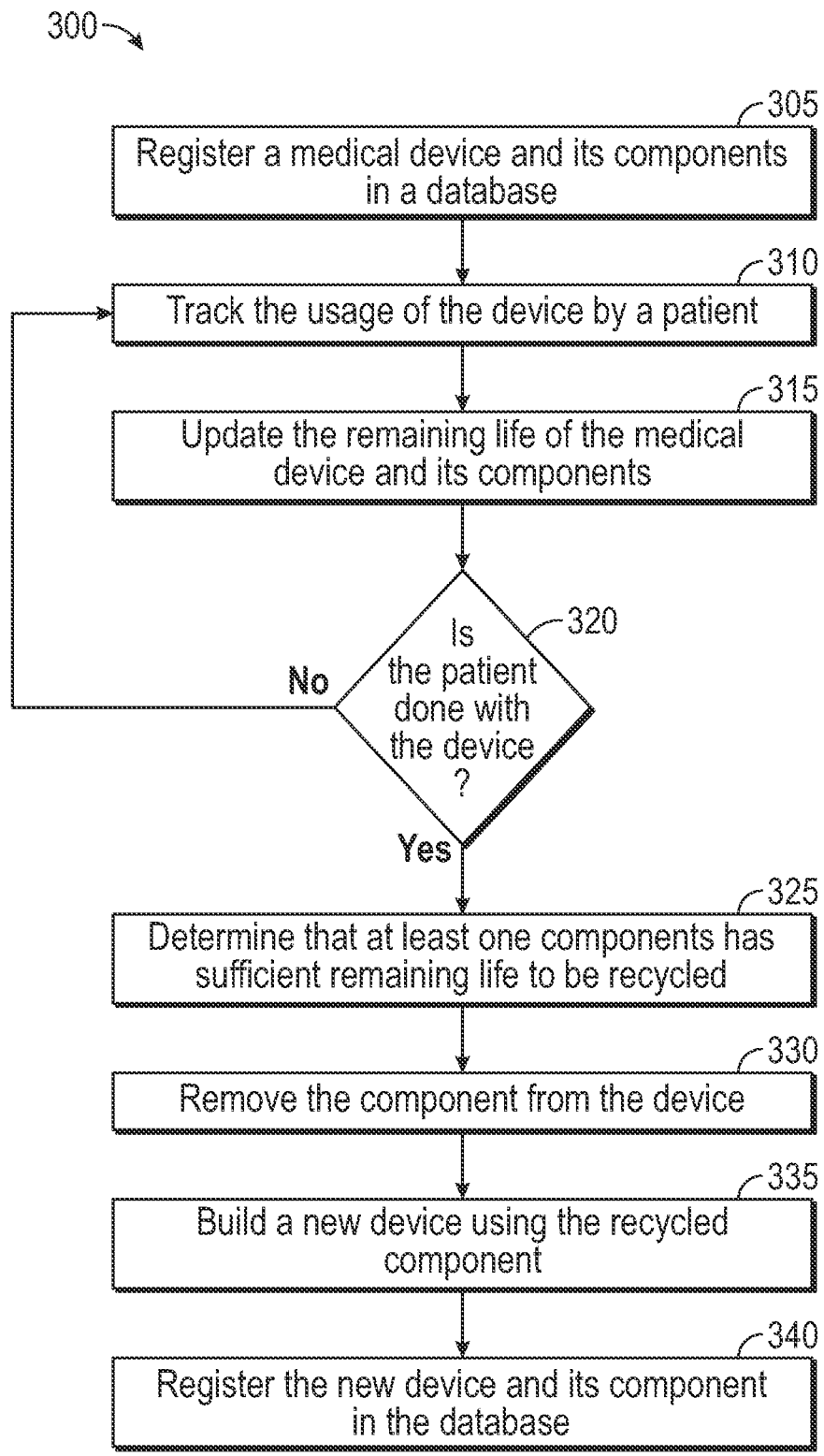
FIG. 3 is a flowchart for building new devices from recycled components, according to one embodiment.

FIG. 3 is a flowchart of a method 300 for building new devices from recycled components, according to one embodiment. At block 305, the device manager (e.g., the device manager 115 in FIG. 1) registers a medical device and its components in a database (e.g., the tracker database 120). The device manager may register the device in response to a prompt from the healthcare facility or a healthcare provider. For example, when receiving a new medical device from the manufacturer, the healthcare facility can send the ID of the device (e.g., a serial number) to the device manager. Or the healthcare facility may scan a QR code on the device that contains the ID of the device. This information can then be forwarded to the device manager to create a new device entry in the database for the medical device.

The healthcare facility may also provide the IDs of the components in the medical device to the device manager which can be used to create component entries in the device entry. For example, an employee may copy and send the serial numbers of the components in the device to the device manager, or the serial numbers of the components may be embedded in a QR code on the device.

In another embodiment, the device manager could retrieve the IDs of the components using the ID of the medical device. For example, the device manager may transmit the device ID to the manufacture who may have the component IDs for that device in its own database. The manufacturer can then send the component IDs to the device manager to be stored in the tracker database.

However, it is not necessary that the device manager receives IDs for the components from the healthcare provide or the manufacturer. For example, when registering the medical device, the device manager may know, based on the type of the device, the different components in that device and generate corresponding component entries. The device manager can then assign IDs to the components so they can be tracked when they are recycled and put in different medical devices.

At block 310, the device manager tracks the usage of the device by a patient. For example, the healthcare facility can inform the device manager when the registered medical device is being used by a patient. For example, when providing the medical device to a patient, a healthcare worker may scan a bar code placed on the device, or type in information into a portal, indicating the medical device was assigned to the patient. The healthcare worker can use the same or similar process to inform the device manager when the device is no longer being used by the patient. For a one-time use medical device, this can indicate to the device manager that the medical device is now able to be recycled. However, for multi-use medical devices, the device manager may wait until receiving a confirmation from the healthcare facility that the medical device is being discarded.

The device manager may receive updates about the usage of a medical device at different time intervals. For example, the healthcare facility may inform device manager on a daily basis whether the medical device was, or was not used, by the patient. For example, the patient may use the breathing apparatus for two days, but then not for the next two days, but then start using the breathing apparatus for the next three days. By receiving daily updates, the device manager knows the breather apparatus was used for five of the last seven days.

In another example, the healthcare facility may tell the device manager when the patient begins using the medical device but then provide no further updates until the patient stops using the device. The device manager may then assume the use of the device was continuous throughout the time frame.

At block 315, the device manager updates the remaining life of the medical device and its components based on the usage of the device. As shown in FIG. 2, the device entry 125 can store the device lifetime 205 as well as the component lifetimes 210, which may represent the expected or desired lifetime of the medical device and its components. The device manager can subtract the usage of the device from these lifetimes to determine the remaining lifetime of the medical device and its components.

In another embodiment, the device manager may use a lifetime prediction algorithm that considers additional factors as well as the usage of the device and the expected or desired lifetimes. These algorithms can consider factors such as the environment (humidity or temperature), damage to the devices, usage patterns, and the like to predict the remaining life of the device and its components. In any case, the embodiments herein are not limited to any particular technique for predicting the remaining life of the device and its components based on tracking the usage of that device.

At block 320, the device manager determines whether the patient is done with the device. That is, the method 300 assumes the medical device is a one-time use device that is then discarded once the patient no longer uses it. However, if the device is a multi-use device, then the query at block 320 may be whether the healthcare facility has determined to discard the device. In any case, if the medical device is still being used, the method 300 returns to block 310 where the device manager continues to track its usage and update the remaining life of the device and its components.

If, however, the patient is done with the device and it is ready to be recycled, the method 300 proceeds to block 325 where the device manager determines that at least one component has remaining life. For example, due to sanitation concerns or the policies of a payor, it may not be permitted to reuse the medical device by giving it another patient. However, it may be permitted to recycle some of the components in the medical device which then can be used to build new medical devices.

At block 325, the device manager confirms that at least one component in the medical device has sufficient remaining life. In one embodiment, a component is eligible to be recycled if it has at least some remaining life. If not, this means the components have been used at or beyond their expected lifetimes, in which case, they may be susceptible to breaking, malfunctioning, or having sanitation issues. As such, the components may not be eligible for recycling.

In one embodiment, the device manager may consider components for recycling only if they have a threshold amount of life remaining. For example, the device manager may recycle a component only if has at least 50% of its remaining life remaining. In another example, the device manager may recycle a component only if it's remaining life is equal to or greater than the expect lifetime of a new medical device. For example, if the desired lifetime of a new breathing apparatus is one year, but an electric motor in an old breathing apparatus has only ten months of remaining life, the device manager may mark the electric motor as ineligible for recycling since it might reduce the lifetime of a new breathing apparatus that includes the motor from one year to ten months. That way, the recycled component does not prematurely lower the expected lifetime of the new medical device it is put in. This can ensure the lifetime of new medical devices with recycled components has the same expected lifetime of new medical devices received from the manufacturer.

However, in other embodiments, it may be acceptable to use recycled components in new devices that may lower their expected lifetimes relative to a new device with all new components. For example, if using recycled components reduces the expected lifetime of the new medical device by less than 10%, this may be an acceptable tradeoff in order to obtain the benefit of using recycled components.

After determining which of the components in the medical device are going to be recycled, the entry for the medical device in the database may be deleted, or flagged to indicate the device has been recycled or discarded.

At block 330, the component is removed from the device. In one embodiment, an employee at the healthcare provider may remove the component or components selected to be recycled from medical device. In another example, the healthcare facility may ship the product to a third-party which removes the component on behalf of the healthcare provider. For example, the third-party may specialize in assembling new medical devices from recycled parts. The third-party may be the manufacturer who builds brand new medical devices or a different party.

At block 335, the healthcare provider or a third-party builds a new device using the recycled component. The new device may include only recycled components (which may have been recycled from multiple old devices) or can include a mix of brand new and recycled components. For example, some parts in the medical device may not be eligible to be recycled, such as a filter. Those parts may always be new parts while other parts can be recycled components.

At block 340, the device manager registers the new device and its components in the database. The new medical device may have a new ID so it can be uniquely tracked. However, the recycled components in the device may use the same ID they had in the previous device entry in the database. This way, the database can track the components as they move between multiple medical devices. Further, when recycling a component, the device manager can update the expected or desired life of that component to match the remaining life that component has in the previous device entry. For example, the electric motor, when new, may have an expected lifetime of two years; however, six months of that lifetime was spent when the motor was in the previous medical device so that the remaining lifetime of the motor is 1.5 years. After being recycled, the expected lifetime of the motor when in the new medical device is 1.5 years. In this manner, as a component is recycled, the device manager can track its expected and remaining lifetime across multiple devices.

FIG. 4 illustrates a device entry 125 in the tracker database 120 in FIG. 1, according to one embodiment. The device entry 125 is the same as the device entry 125 in FIG. 2 except the addition of columns 405 and 410. The column 405 indicates whether a particular component in the medical device (i.e., Medical Device A) is recyclable or not. That is, the device entry 125 illustrates an example where the tracker database can track components that are, and are not, recyclable. However, in other embodiments, the device entry 125 may track only components that are recyclable. In that case, the column 405 would not be used since it is assumed every modular component listed in the device entry 125 is recyclable.

In this example, all the components are recyclable except for the component entry 135F corresponding to a filter in Medical Device A. For sanitation or other reasons, the filter cannot be recycled, no matter the amount of remaining life. The device entry 125 can track the component usage 220E and the remaining life 140E of the filter, but this may be to determine when the filter should be replaced as part of a maintenance schedule or algorithm, rather than determining whether the filter can be recycled when the Medical Device A is being discarded.

The column 410 indicates whether a particular component requires sterilization before it can be reused in a new medical device. In this case, the component entries 135A and 135C indicate the face apparatus and the ventilator require sterilization while the entries 135B and 135D indicate the electric motor and the oxygen supply do not. The cost and time required to perform sterilization can be used to adjust the remaining life for those components, which is discussed in more detail in FIG. 5.

Figure 5:
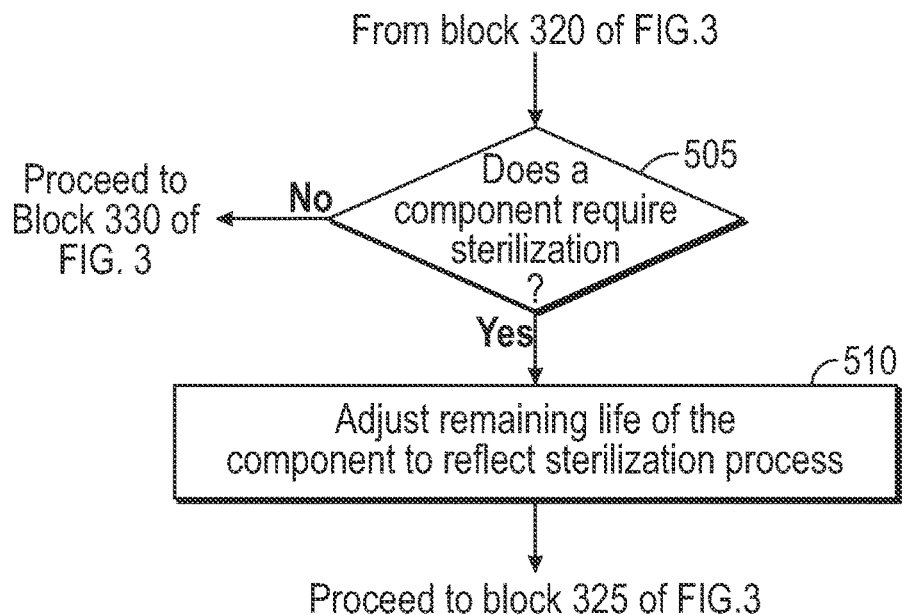
FIG. 5 is a flowchart for adjusting the remaining life of a component based on a sterilization process, according to one embodiment.

FIG. 5 is a flowchart of a method 500 for adjusting the remaining life of a component based on a sterilization process, according to one embodiment. The method 500 can begin after block 320 of FIG. 3. At block 505, the device manager determines whether any component in the medical device requires sterilization. As shown in FIG. 4, the device entry in the tracker database can indicate which components needs sterilization and which do not.

If none of the components require sterilization, then the method 500 proceeds to block 330 of FIG. 3 to proceed as discussed above. However, for the components that do require sterilization, the method 500 proceeds to block 510 where the device manager adjusts the remaining life of the component (or components) to reflect the sterilization process. For example, the sterilization process may have a negative impact of the remaining life of the component such as causing more wear and tear. As such, the sterilization process can reduce the life of the product, and in response, the device manager and reduces its remaining life (e.g., reduce the life by a two or three months). In another example, the sterilization process can add an additional cost to the recycling process. This additional cost can be reflected in the remaining life. For example, the remaining life stored in the component entry in the database may indicate the component has another two years of life, but due to the cost of the sterilization process, the device manager may artificially consider its remaining life to be lower (e.g., only 1.5 years).

After the remaining life has been adjusted to reflect the sterilization process, the method 500 proceeds to block 325 of FIG. 3 to determine whether it is worth recycling the component. For instance, the remaining life stored in the tracker database may exceed a threshold which qualifies the component to be recycled. However, after adjusting the remaining life based on the sterilization process at block 510, the adjusted remaining life may be below the threshold, which means the component no longer qualifies to be recycled. In this manner, sterilization can be used by the device manager to adjust the remaining life and then determine whether the component should be recycled as discussed in FIG. 3.

Figure 6:
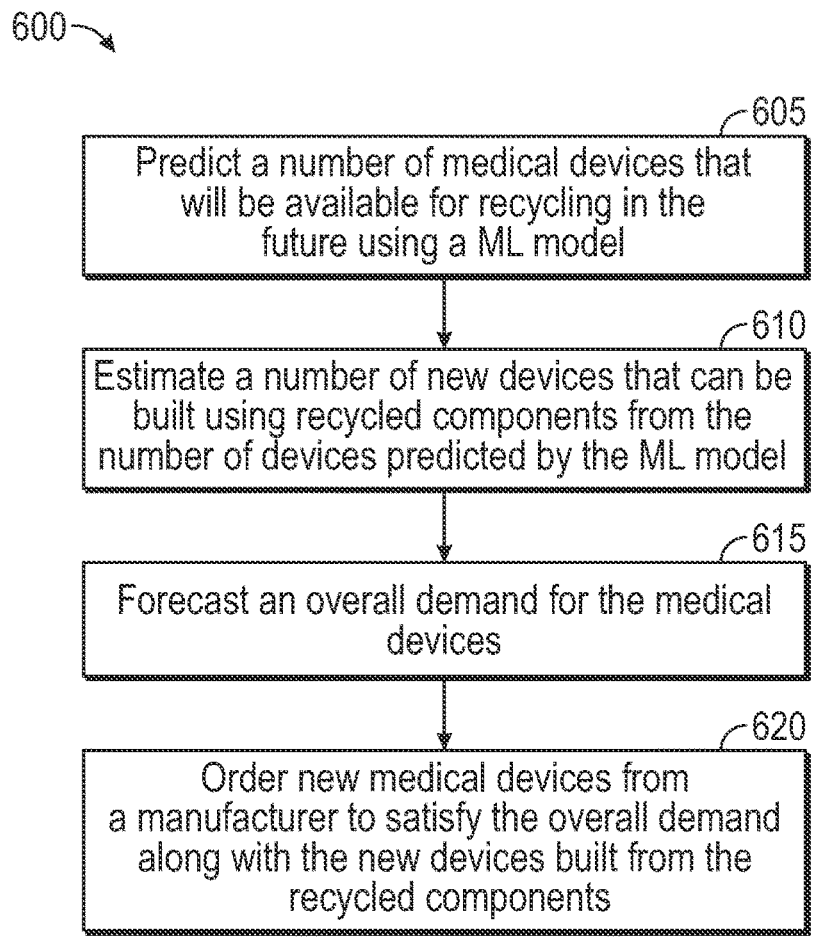
FIG. 6 is a flowchart for predicting future supply of devices having components that can be recycled, according to one embodiment.

FIG. 6 is a flowchart of a method 600 for predicting future supply of devices having components that can be recycled, according to one embodiment. At block 605, the demand predictor predicts a number of medical devices that will be available for recycling in the future using a ML model. In one embodiment, the ML model predicts, based on the current use of the medical devices, how many of those devices will no longer be used by patients, and thus, eligible to be recycled (assuming those devices are one-time use medical devices). The ML model can predict how many devices will be available in a particular time range (e.g., in a month, or in the next two weeks). The details for using an ML model to predict the future supply of devices is discussed in FIG. 7.

At block 610, the demand predictor estimates a number of new devices that can be built using recycled components from the number of devices predicted by the ML model at block 605. For example, the ML model can identify specific devices it predicts will be available in the future. The demand predictor can view the entries in the tracker database for those devices to determine whether any components in those devices will have a remaining life that qualifies them to be recycled (as discussed in FIG. 3). From this, the demand predictor can estimate how many components (and their types) will be available for recycling.

The demand predictor can also consider the amount of new components in its current inventory. For example, the new devices may be assembled using both recycled and new components. Once this information is determined, the demand predictor can estimate how many new devices can be assembled using the recycled and new components.

At block 615, the demand predictor forecasts an overall demand for the medical devices. This forecast can be for a particular healthcare facility or for a plurality of healthcare facilities that may be operated by the same healthcare provider. The forecast can be based on any type of forecasting technique, such as evaluating historical demand for the medical devices. In any case, the forecast indicates how many devices the healthcare facility will need at a future time (e.g., within the next month or two weeks). This future time can coincide with the prediction made by the ML model at block 605 of how many devices will be ready from recycling at the same future time.

At block 620, the demand predictor orders new medical devices from a manufacture to satisfy the overall demand along with the new devices built from the recycled components. In one embodiment, the demand predictor subtracts the number of medical devices that can be assembled from recycled components from the overall demand to identify the number of new medical devices that should be ordered from the manufacturer. Thus, the combination of new devices assembled using recycle components and new devices ordered from the manufacture should satisfy the total overall demand for the medical devices at a future date. In this manner, the demand predictor can use the ML model to predict a supply of new medical devices that can be produced from recycled components that can offset the number of new medical devices that are ordered from the manufacturer to satisfy overall demand for the medical devices.

Figure 7:
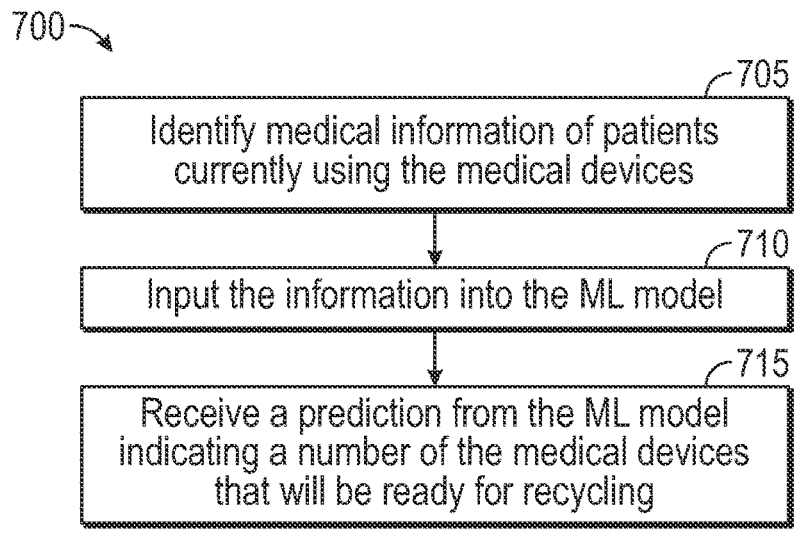
FIG. 7 is a flowchart for predicting future supply of devices using a machine learning model, according to one embodiment.

FIG. 7 is a flowchart of a method 700 for predicting future supply of devices using a machine learning model, according to one embodiment. In one embodiment, the method 700 is one example of performing block 605 to predict a number of medical devices that will be available for recycling in the future.

At block 705, the demand predictor identifies medical information of a patient currently using a medical device. This medical information can include age, medical history, biometric information, and the like. The medical information can also indicate the diagnosis that resulted in the use of the medical device. For example, the patient may be diabetic, but the patient may be currently experiencing hypoxemia which results in the patient being given a breathing apparatus. The hypoxemia may be the diagnosis or issue that results in the patient being assigned the medical device.

At block 710, the demand predictor inputs the medical information for the patient into the ML model. As discussed later, the ML model can be trained to predict how long a particular patient, based on their medical information, will use the medical device. The ML model can receive the medical information for multiple patients to predict how long each patient will likely use the medical devices.

At block 715, the demand predictor receives a prediction from the ML Model indicating a number of the medical devices that will be ready for recycling by a future date. For example, the ML model can output a likelihood that the patient will stop using the medical device by the future date. If the likelihood is above a threshold (e.g., 90%) the ML model assumes the device will be available. In this manner, the ML model can evaluate all the medical devices currently in use to provide the demand predictor with an estimate of how many of those medical devices will no longer be in use at a defined, future date or time range (e.g., within the next month).

Figure 8:
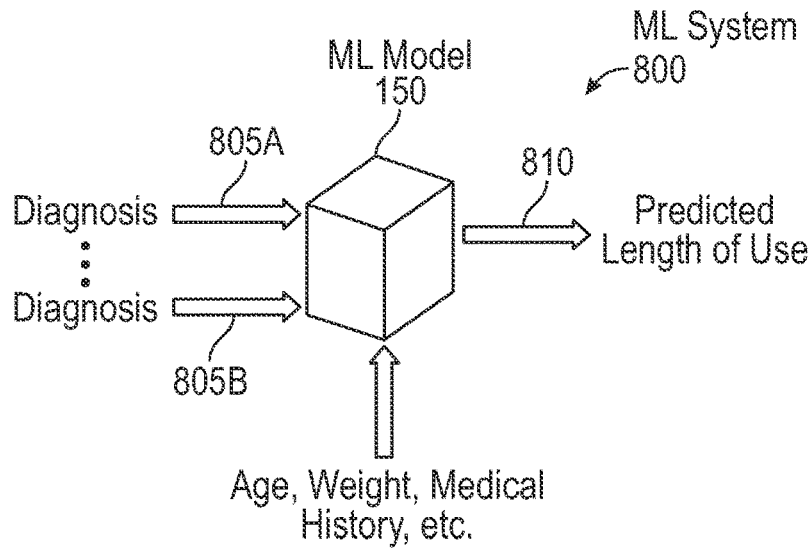
FIG. 8 illustrates a machine learning system for predicting future supply of devices, according to one embodiment.

FIG. 8 illustrates a ML system 800 for predicting future supply of devices, according to one embodiment. The ML system 800 is one example of a ML system that can be used to perform the method 700 in FIG. 7. As shown, the ML model 150 predicts the length of use a patient will use a medical device. Moreover, the ML model 150 can receive multiple diagnoses 805 for the patient. For example, the patient may have both heart disease and diabetes. As such, the ML model 150 can receive multiple diagnoses as inputs.

In one embodiment, the diagnoses 805 are provided by a parser which scans the patient's medical records. However, in other embodiments, the diagnoses 805 can be provided to the ML model 150 by the patient or the healthcare professional.

Using the diagnosis 805 as an input, the ML model 150 predicts the length of use 810 such as a date or time range when the ML model 150 predicts, with sufficient confidence, that the patient will no longer need the medical device (e.g., the patient has recovered). Stated differently, the length of use 810 can be the length of time required before the patient will be healed and does not need the medical device. The length of use 810 can change depending on the type of diagnosis 805 as well as the combination of diagnoses 805. For example, the ML model 150 may determine that the length of use 810 for Diagnosis A is 10 days, but the length of use 810 for Diagnosis B is 14 days. If the patient has both Diagnoses A and B, the length of use 810 may be predicted as 18 days. Thus, the ML model 150 can predict the length of stay in response to one diagnosis, or a combination of several diagnoses.

As described later, the ML model 150 can be trained using historical medical records for patients. These records can indicate the diagnoses of these patients as well as their length of use of using the same medical device as the current patient being evaluated. From this, the ML model 150 can learn correlations between a particular diagnosis (or a combination of diagnoses) and the length of use of a medical device. This is discussed in more detail in FIGS. 9 and 10.

In addition to using the diagnosis 805 as an input, the ML system 800 indicates the ML model 150 can also consider other factors to predict the length of use 810. For example, the ML model 150 may use the patient's age, weight, medical history, ethnicity, and the like since these factors may also affect how long it takes a patient to recover. For example, the ML model 150 may predict a longer use of the medical device for an older patient who has the same diagnosis as a younger patient. Or the patient's weight or a history of previous diagnoses can result in the ML model 150 predicting a different length of use 810 than if these factors were not input into the ML model 150.

Figure 9:
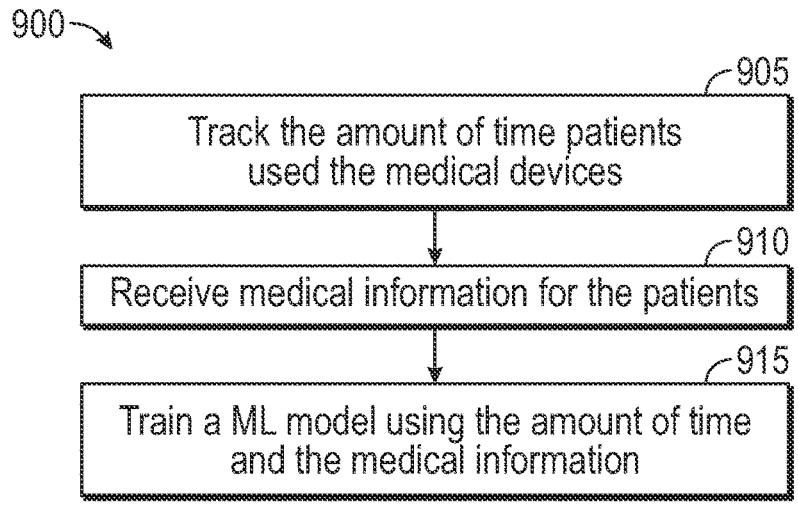
FIG. 9 is a flowchart for training a machine learning model to predict future supply of devices, according to one embodiment.

FIG. 9 is a flowchart of a method 900 for training a ML model to predict future supply of devices, according to one embodiment. That is, the method 900 describes techniques that can be used to train a ML model that can predict a number of medical devices that will be available for recycling at a future data as discussed above.

At block 905, a training application (e.g., a software application), tracks the amount of time patients used the medical devices before the devices were no longer needed (e.g., the patients recovered). This information can be turned into training data for the ML model. That is, the training application can track historical usage of the medical devices in order to train the ML model to predict the length of usage for a patient.

At block 910, the training application receives medical information for the patients such as diagnosis (or diagnoses), patients' ages, weights, medical histories, ethnicities, and the like. This information can be identified by parsing the medical records of the patients using an automatic parser, or can be entered manually.

In one embodiment, pre-processing the data in the medical records may improve the ML training process by making the data more compatible with natural language processing, and ultimately for consumption by the ML model during training. Pre-processing can include tokenization where strings of text are split into smaller strings or "tokens." For example, paragraphs can be tokenized into sentences and sentences can be tokenized into words. Pre-processing can also include normalization to, e.g., converting all characters to lowercase, converting accented characters to ASCII characters, expand contractions, convert words to numeric form, etc. Pre-processing can also include noise removal such as removing extra white spaces, HTML tags, etc. Pre-processing can also include lemmatization or stemming where a word is converted to its base form such as "holding" to "hold." Pre-processing can further include text identification and text elimination of redundant words or the reduction of a sentence or phrase to the portions that are most suitable for machine learning training or application, e.g. elimination of verbs, conjunction or other extraneous words and/or reducing a phrase or sentence to its most relevant bigram or root during any relevant steps of machine learning training and/or application. Pre-processing can further include any other suitable technique for making text ingestion (either in a training phase of an ML or with respect to data ingested after training to render a prediction).

In one embodiment, the pre-processed text is converted into an object that can be represent numerically. For example, one-hot encodings and word embedding vectors can be used. The resulting object can then be processed by the natural language processing algorithm to improve its ability to identify the diagnosis and the length of stay. Improving the results of the natural language processing algorithm can have a positive impact on the accuracy of training the ML model.

At block 915, the training application trains the ML model using the amount of time determined at block 905 and the medical information received at block 910. For example, the training application can adjust the weights in the ML model based on making predictions using the medical information and then determining whether those predictions matched the actual usage of the medical devices for the patients.

Figure 10:
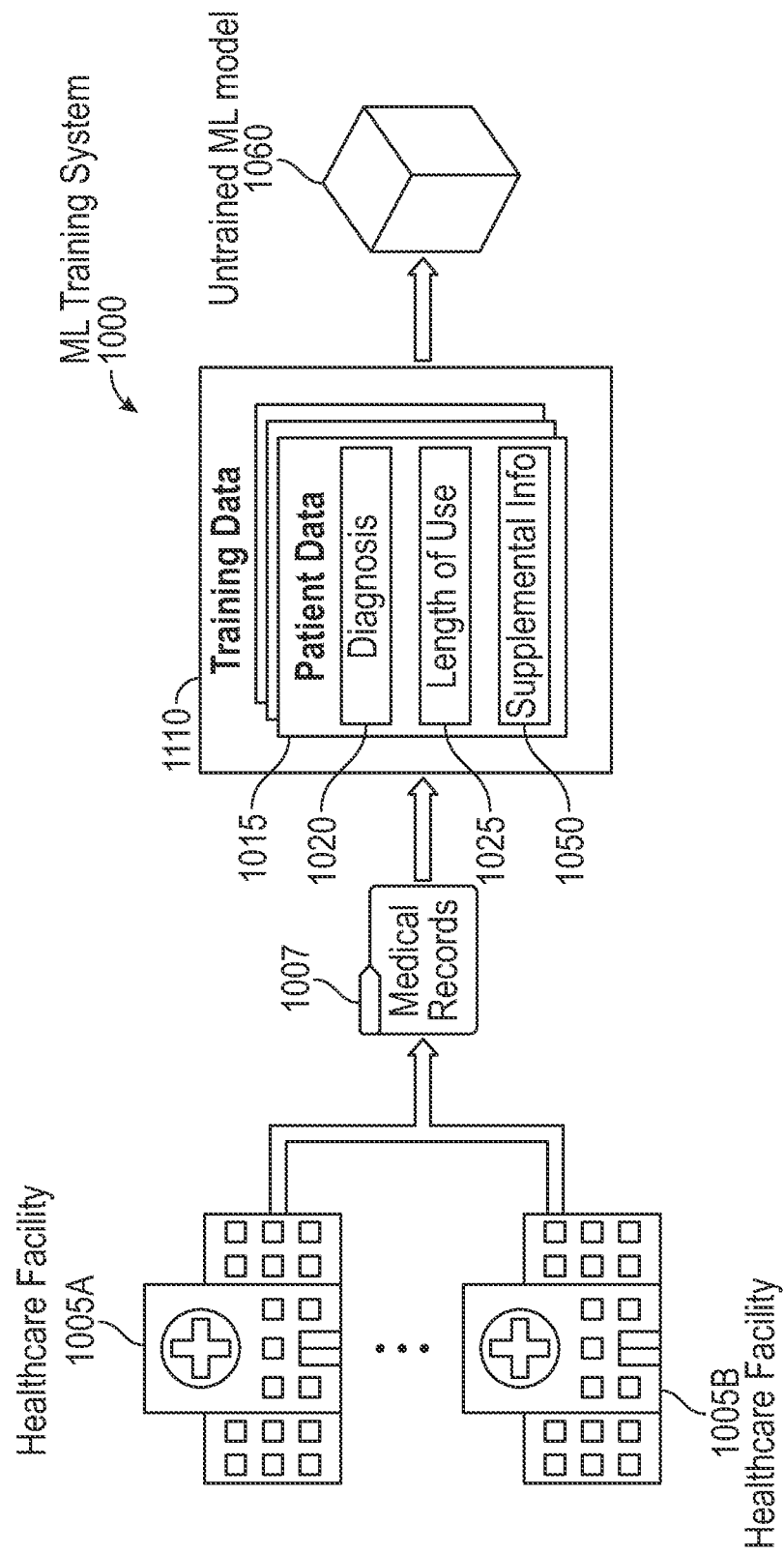
FIG. 10 is a system for training a machine learning model, according to one embodiment.

FIG. 10 is a system 1000 for training a ML model, according to one embodiment. The ML system 1000 is one example of a ML system that can be used to perform the method 900 in FIG. 9. The left of the ML training system 1000 illustrates collecting medical records 1007 from patients admitted into multiple healthcare facilities 1005. That is, the medical records 1007 can be associated with multiple patients previously admitted into multiple facilities 1005. In one embodiment, the medical records 1007 are for patients that have been assigned a medical device for use at, or by, the healthcare facilities 1005 but are no longer using the medical device.

Because the medical records 1007 are used to trained an untrained ML model 1060, the ML training system 1000 may redact personal information from the medical records 1007. For example, because the ML model 1060 is being trained to learn the correlation between diagnosis (and potentially other information) and the length of use of a medical device, the personal information of the patients such as their names, phone numbers, addresses, etc. may be unnecessary. Thus, this information can be redacted or removed from the medical records 1007 to improve security and provide anonymity.

While the ML training system 1000 illustrates collecting medical records 1007 from multiple facilities, the system 1000 could train the ML model 1060 using medical records 1007 from just one facility. However, this may require collecting medical records over a longer period of time to have sufficient training data 1010. Moreover, it may lead to a better trained model if the medical records 1007 are collected from facilities that are in different geographic areas. Alternatively, it may be better if the ML model 1060 is trained using medical records 1007 from the same geographic region as the patient being evaluated in method 700. For example, the demand predictor may have several ML models that are trained using medical records 1007 collected from different geographic regions in a country. Depending on the location of the current patient being evaluated at method 700, the demand predictor may select the ML model trained using medical records gathered from the same geographic region in order to predict the length of use of the medical device.

The ML training system 1000 generates training data 1010 using the medical records 1007. In this example, the training data 1010 includes patient data 1015 for each patient identified in the medical records 1007. The patient data 1015 indicates the diagnosis 1020 (or diagnoses) of the patient that was being treated at the healthcare facility 1005 and the patient's length of use 1025 of the medical device. Thus, unlike in method 700 where the ML model predicts the length of use, here the length of use 1025 is a known factor so that, when the patient data 1015 is input into the untrained ML model 1060, it can learn the correlation between a particular diagnosis (or a combination of diagnoses) and the length of use 1025 of the medical device.

Optionally, the patient data 1015 can include supplemental information 1030, such as the patient's age, weight, medical history, ethnicity, and the like since these factors may also affect how long it takes a patient to recover. In one embodiment, the supplemental information can also include the type of the healthcare facilities 1005 being evaluated. For example, when being trained, the ML model 1060 may learn that patients may heal quicker for the same disease at different types of healthcare facilities. Thus, the ML model may predict that the length of use of the medical device at a hospital is different than the length of use of the medical device of the same patient with the same diagnosis at a skilled nursing center.

However, identifying the supplemental information 1030 from the medical records 1007 is not a requirement. That is, the ML model 1035 can be trained solely using the diagnosis 1020 and the length of use 1025.

In one embodiment, the ML training system 1000 may generate training data only for the patients that were discharged rather than those that passed away while in the healthcare facility 1005. That is, the training data 1010 may include only the patients who recovered from the diagnosis 1020.

The right side of FIG. 10 illustrates training the ML model 1060 using the training data. As a result of training the model 160, the ML training system 1000 can generate a trained ML model (e.g., the ML model 150 in FIG. 1) that can be used during an inference stage to predict a length of use of a medical device for a patient based on any number of factors such as the patient's diagnosis, age, weight, and the like.

Figure 11:
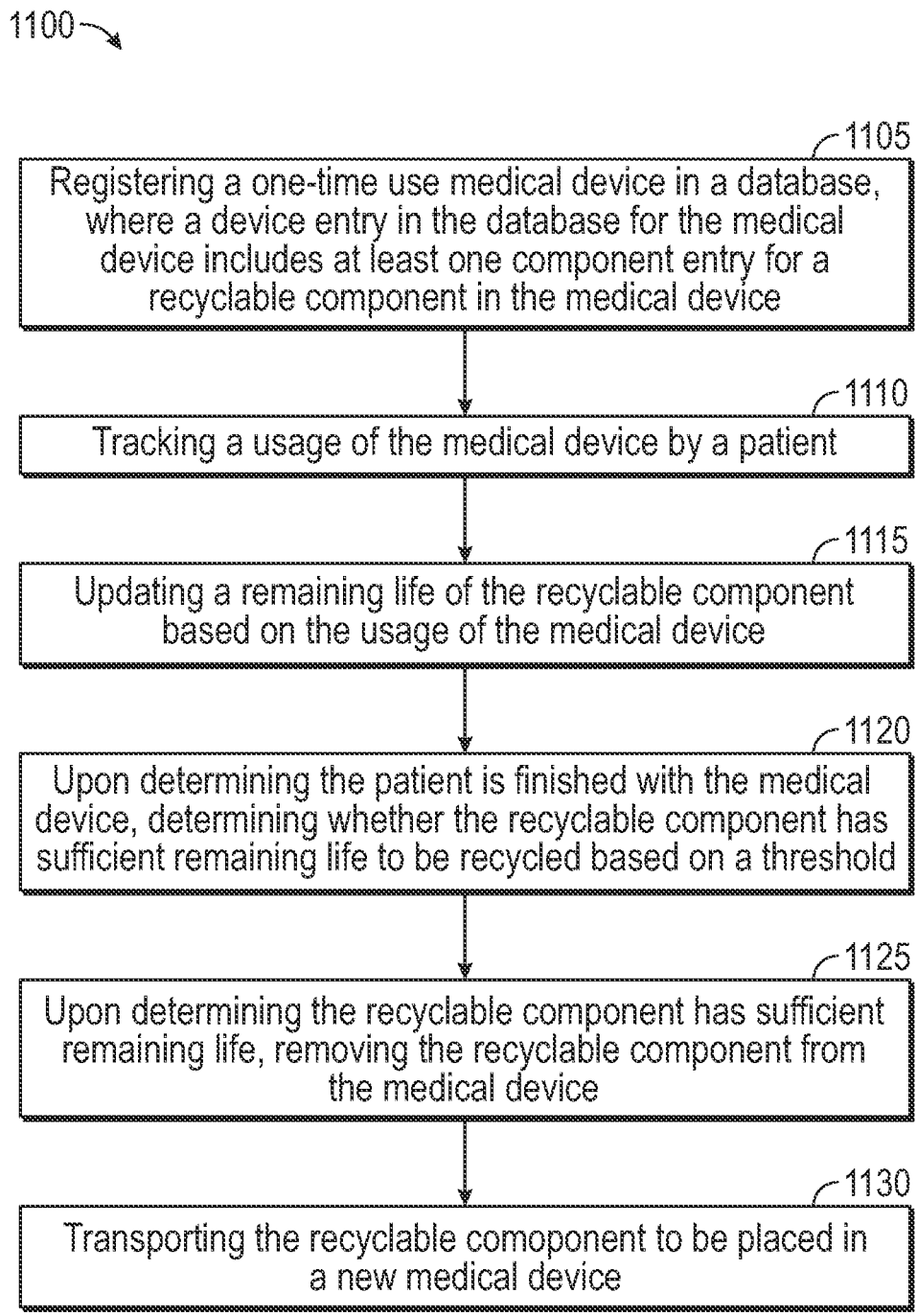
FIG. 11 is a flowchart for building new devices from recycled components, according to one embodiment.

FIG. 11 is a flowchart of a method 1100 for building new devices from recycled components, according to one embodiment. At block 1105, a device manager (e.g., the device manager 115 in FIG. 1) registers a one-time use medical device in a database, where a device entry in the database for the medical device includes at least one component entry for a recyclable component in the medical device. This block can include the same discussion related to block 305 of FIG. 3.

At block 1110, the device manager tracks a usage of the medical device by a patient. This block can include the same discussion related to block 310 of FIG. 3.

At block 1115, the device manager updates a remaining life of the recyclable component based on the usage of the medical device. This block can include the same discussion related to block 315 of FIG. 3.

At block 1120, upon determining the patient is finished with the medical device, the device manager determines whether the recyclable component has sufficient remaining life to be recycled based on a threshold. This block can include the same discussion related to blocks 320 and 325 of FIG. 3.

At block 1125, upon determining the recyclable component has sufficient remaining life, the device manager outputs instructions to remove the recyclable component from the medical device. This block can include the same discussion related to block 330 of FIG. 3.

At block 1130, the device manager outputs instructions to transport the recyclable component to be placed in a new medical device. This can include moving the recyclable component to a department in the healthcare provider that builds the new medical device using the recyclable component, or shipping the recyclable component to a third-party who then builds the new medical device. This block can include the same discussion related to block 335 of FIG. 3.

Example Computing Hardware

Figure 12:
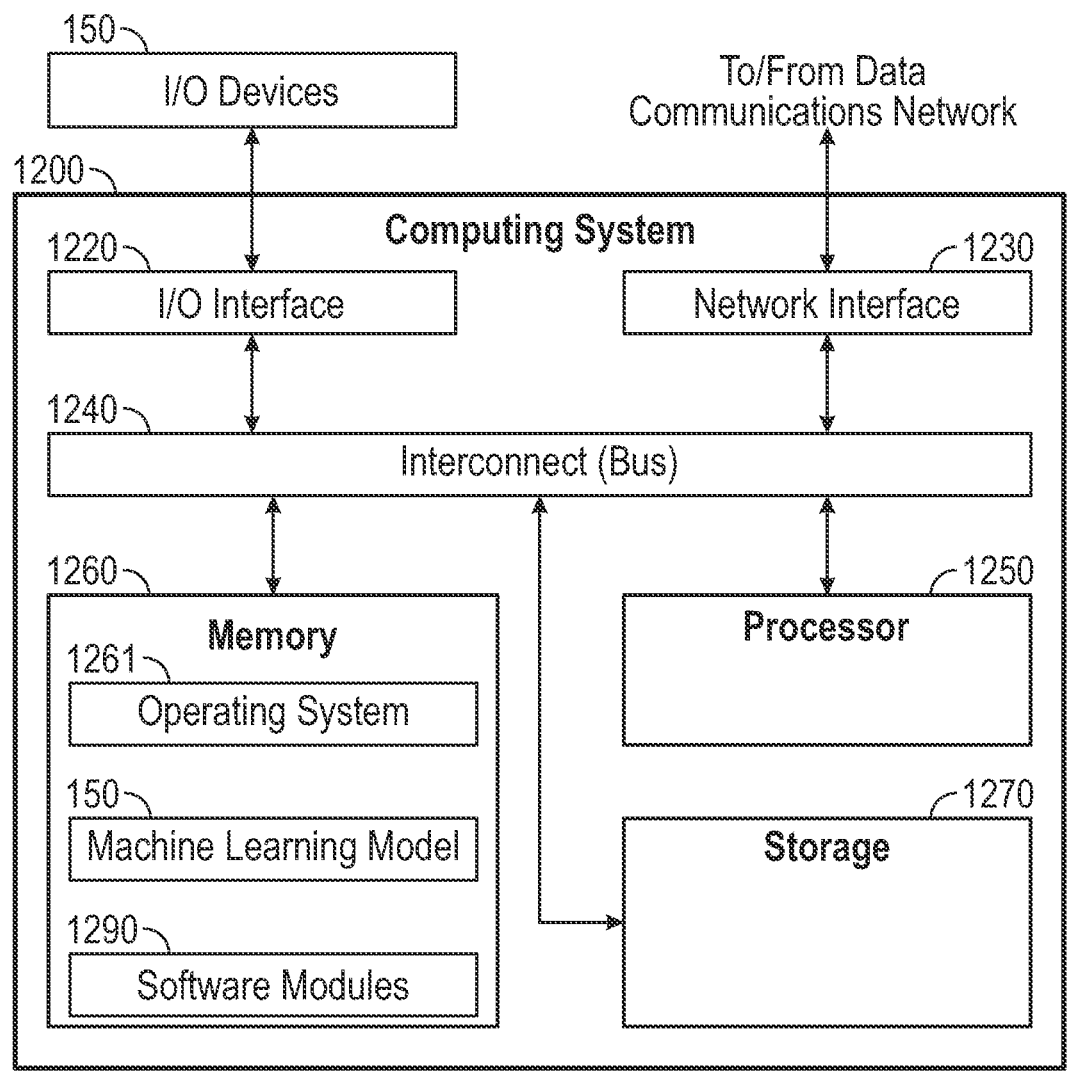
FIG. 12 illustrates a computing system, according to one embodiment.

FIG. 12 illustrates a computing system 1200, which may be used to implement the device manager in FIG. 1 (e.g., a computer, a laptop, a tablet, a smartphone, web server, data center, cloud computing environment, etc.), or any other computing device described in the present disclosure. As shown, the computing system 1200 includes, without limitation, a computer processor 1250 (e.g., a central processing unit), a network interface 1230, and memory 1260. The computing system 1200 may also include an input/output (I/O) device interface 1220 connecting I/O devices 1280 (e.g., keyboard, display and mouse devices) to the computing system 1200.

The processor 1250 retrieves and executes programming instructions stored in the memory 1260 (e.g., a non-transitory computer readable medium). Similarly, the processor 1250 stores and retrieves application data residing in the memory 1260. An interconnect 1240 facilitates transmission, such as of programming instructions and application data, between the processor 1250, I/O device interface 1220, storage 1270, network interface 1230, and memory 1260. The processor 1250 is included to be representative of a single processor, multiple processors, a single processor having multiple processing cores, and the like. And the memory 1260 and the storage 1270 are generally included to be representative of volatile and non-volatile memory elements. For example, the memory 1260 and the storage 1270 can include random access memory and a disk drive storage device. Although shown as a single unit, the memory 1260 or the storage 1270 may be a combination of fixed and/or removable storage devices, such as magnetic disk drives, flash drives, removable memory cards or optical storage, network attached storage (NAS), or a storage area-network (SAN). The storage 1270 may include both local storage devices and remote storage devices accessible via the network interface 1230. One or more ML models 150 are maintained in the memory 1260 to predict the length of stay of a patient at a healthcare facility. Additionally, one or more software modules 1290 may be maintained in the memory to perform the functions of a parser, training application, demand predictor, or other applications discussed above.

Further, the computing system 1200 is included to be representative of a physical computing system as well as virtual machine instances hosted on a set of underlying physical computing systems. Further still, although shown as a single computing device, one of ordinary skill in the art will recognize that the components of the computing system 1200 shown in FIG. 12 may be distributed across multiple computing systems connected by a data communications network.

As shown, the memory 1260 includes an operating system 1261. The operating system 1261 may facilitate receiving input from and providing output to various components. In another example, the network interface 1230 can be used to receive medical records from patients who have been discharged in order to train the ML model 150 as discussed in method 900.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

Clause 1: A method comprising registering a one-time use medical device in a database, wherein a device entry in the database for the medical device includes at least one component entry for a recyclable component in the medical device; tracking a usage of the medical device by a patient; updating a remaining life of the recyclable component based on the usage of the medical device; upon determining the patient is finished with the medical device, determining whether the recyclable component has sufficient remaining life to be recycled based on a threshold; upon determining the recyclable component has sufficient remaining life, removing the recyclable component from the medical device; and transporting the recyclable component to be placed in a new medical device.

Clause 2: In addition to the clause 1, wherein the device entry for the medical device comprises a second component entry for a second recyclable component in the medical device, the method further comprising: upon determining the patient is finished with the medical device, determining that the second recyclable component does not have sufficient remaining life to be recycled based on the threshold, wherein the second recyclable component is discarded.

Clause 3: In addition to the clause 1 or 2, further comprising: registering the new medical device built using the recyclable component in the database, wherein a device entry in the database for the new medical device includes at least one component entry for the recyclable component indicating the recyclable component has an component lifetime that matches the remaining life of the recyclable component when the patient was finished with the medical device.

Clause 4: In addition to the clause 1, 2, or 3, wherein the at least one component entry for the recyclable component stores a component lifetime indicating an expected lifetime of the recyclable component, a component usage time of the recyclable component, and the remaining life of the recyclable component.

Clause 5: In addition to the clause 4, wherein the at least one component entry for a recyclable component stores an indicator indicating whether the recyclable component should undergo a sterilization process before being recycled into the new medical device.

Clause 6: In addition to the clause 5, further comprising, before determining whether the recyclable component has sufficient remaining life to be recycled: adjusting the remaining life of the recyclable component based on the sterilization process.

Clause 7: In addition to the clause 1, 2, 3, 4, 5, or 6, further comprising: predicting a number of medical devices that will be available for recycling in the future using a machine learning (ML) model by: inputting medical information for a plurality of patients currently assigned a plurality of medical devices; and receiving indications from the ML model predicting which of the plurality of medical devices will no longer be used by the plurality of patients by a future date.

Clause 8: In addition to the clause 7, further comprising: estimating a number of new medical devices that can be built using recycled components from the number of medical devices predicted by the ML model.

Clause 9: In addition to the clause 7, further comprising, before predicting the number of medical devices that will be available for recycling in the future: tracking an amount of time a second plurality of patients used a second plurality of medical devices; receiving medical information for the second plurality of patients; and training the ML model using the amount of time and the medical information.

Clause 10: A non-transitory computer readable medium comprising instructions to be executed in a processor, the instructions when executed in the processor perform an operation, the operation comprising: registering a one-time use medical device in a database, wherein a device entry in the database for the medical device includes at least one component entry for a recyclable component in the medical device; tracking a usage of the medical device by a patient; updating a remaining life of the recyclable component based on the usage of the medical device; upon determining the patient is finished with the medical device, determining whether the recyclable component has sufficient remaining life to be recycled based on a threshold; upon determining the recyclable component has sufficient remaining life, outputting instructions to remove the recyclable component from the medical device; and outputting instructions to transport the recyclable component to be placed in a new medical device.

Clause 11: In addition to the clause 10, wherein the device entry for the medical device comprises a second component entry for a second recyclable component in the medical device, the operation further comprising: upon determining the patient is finished with the medical device, determining that the second recyclable component does not have sufficient remaining life to be recycled based on the threshold, wherein the second recyclable component is discarded.

Clause 12: In addition to the clause 10 or 11, the operation further comprising: registering the new medical device built using the recyclable component in the database, wherein a device entry in the database for the new medical device includes at least one component entry for the recyclable component indicating the recyclable component has an component lifetime that matches the remaining life of the recyclable component when the patient was finished with the medical device.

Clause 13: In addition to the clause 10, 11, or 12, wherein the at least one component entry for the recyclable component stores a component lifetime indicating an expected lifetime of the recyclable component, a component usage time of the recyclable component, the remaining life of the recyclable component, and an indicator indicating whether the recyclable component should undergo a sterilization process before being recycled into the new medical device.

Clause 14: In addition to the clause 13, the operation further comprising, before determining whether the recyclable component has sufficient remaining life to be recycled: adjusting the remaining life of the recyclable component based on the sterilization process.

Clause 15: In addition to the clause 10, 11, 12, 13, or 14, the operation further comprising: predicting a number of medical devices that will be available for recycling in the future using a ML model by: inputting medical information for a plurality of patients currently assigned a plurality of medical devices; and receiving indications from the ML model predicting which of the plurality of medical devices will no longer be used by the plurality of patients by a future date; and estimating a number of new medical devices that can be built using recycled components from the number of medical devices predicted by the ML model.

Clause 16: In addition to the clause 15, the operation further comprising, before predicting the number of medical devices that will be available for recycling in the future: tracking an amount of time a second plurality of patients used a second plurality of medical devices; receiving medical information for the second plurality of patients; and training the ML model using the amount of time and the medical information.

Clause 17: A system, comprising: a processor; and memory storing code which, when executed by the processor, performs an operation, the operation comprising: registering a one-time use medical device in a database, wherein a device entry in the database for the medical device includes at least one component entry for a recyclable component in the medical device; tracking a usage of the medical device by a patient; updating a remaining life of the recyclable component based on the usage of the medical device; upon determining the patient is finished with the medical device, determining whether the recyclable component has sufficient remaining life to be recycled based on a threshold; upon determining the recyclable component has sufficient remaining life, outputting instructions to remove the recyclable component from the medical device; and outputting instructions to transport the recyclable component to be placed in a new medical device.

Clause 18: In addition to the clause 17, wherein the operation further comprises: registering the new medical device built using the recyclable component in the database, wherein a device entry in the database for the new medical device includes at least one component entry for the recyclable component indicating the recyclable component has an component lifetime that matches the remaining life of the recyclable component when the patient was finished with the medical device.

Clause 19: In addition to the clause 17 or 18, wherein the at least one component entry for the recyclable component stores a component lifetime indicating an expected lifetime of the recyclable component, a component usage time of the recyclable component, the remaining life of the recyclable component, and an indicator indicating whether the recyclable component should undergo a sterilization process before being recycled into the new medical device, wherein the operation further comprises, before determining whether the recyclable component has sufficient remaining life to be recycled: adjusting the remaining life of the recyclable component based on the sterilization process.

Clause 20: In addition to the clause 17, 18, or 19, the operation further comprising: predicting a number of medical devices that will be available for recycling in the future using a ML model by: inputting medical information for a plurality of patients currently assigned a plurality of medical devices; and receiving indications from the ML model predicting which of the plurality of medical devices will no longer be used by the plurality of patients by a future date; and estimating a number of new medical devices that can be built using recycled components from the number of medical devices predicted by the ML model.

What is claimed is:

1. A method, comprising:
   registering a one-time use medical device in a database, wherein a device entry in the database for the medical device includes at least one component entry for a recyclable component in the medical device;
   tracking a usage of the medical device by a patient;
   updating a remaining life of the recyclable component based on the usage of the medical device;
   upon determining the patient is finished with the medical device, determining whether the recyclable component has sufficient remaining life to be recycled based on a threshold;
   upon determining the recyclable component has sufficient remaining life, removing the recyclable component from the medical device;
   transporting the recyclable component to be placed in a new medical device; and
   predicting a number of medical devices that will be available for recycling at a future date using a machine learning (ML) model, wherein the ML model comprises at least one of a neural network, and is trained by:
      tracking an amount of time each of a first plurality of patients used a first plurality of medical devices;
      receiving medical information, including at least a diagnosis, for each of the first plurality of patients; and
      using the amount of time and the medical information to correlate the amount of time and the medical information.

2. The method of claim 1, wherein the device entry for the medical device comprises a second component entry for a second recyclable component in the medical device, the method further comprising:
   upon determining the patient is finished with the medical device, determining that the second recyclable component does not have sufficient remaining life to be recycled based on the threshold, wherein the second recyclable component is discarded.

3. The method of claim 1, further comprising:
   registering the new medical device built using the recyclable component in the database, wherein a device entry in the database for the new medical device includes at least one component entry for the recyclable component indicating the recyclable component has an component lifetime that matches the remaining life of the recyclable component when the patient was finished with the medical device.

4. The method of claim 1, wherein the at least one component entry for the recyclable component stores a component lifetime indicating an expected lifetime of the recyclable component, a component usage time of the recyclable component, and the remaining life of the recyclable component.

5. The method of claim 4, wherein the at least one component entry for a recyclable component stores an indicator indicating whether the recyclable component should undergo a sterilization process before being recycled into the new medical device.

6. The method of claim 5, further comprising, before determining whether the recyclable component has sufficient remaining life to be recycled:
   adjusting the remaining life of the recyclable component based on the sterilization process.

7. The method of claim 1, wherein
   predicting the number of medical devices that will be available for recycling at the future date using the machine learning (ML) model comprises:
   inputting medical information, including at least a diagnosis, for a second plurality of patients that are currently assigned to use a second plurality of medical devices; and
   receiving indications from the ML model predicting which of the second plurality of medical devices will be available for recycling by the future date.

8. The method of claim 1, further comprising:
   determining a number of recycled components from the number of medical devices that will be available for recycling at the future date predicted by the ML model;
   determining a number of new components available for assembling with the number of recycled components to produce a first plurality of new medical devices;
   estimating a number of the first plurality of new medical devices based on the number of recycled components and the number of new components; and
   ordering a second plurality of new medical devices to satisfy an overall demand for new medical devices along with the first plurality of new medical devices built from recycled components.

9. A non-transitory computer readable medium comprising instructions to be executed in a processor, the instructions when executed in the processor perform an operation, the operation comprising:
   registering a one-time use medical device in a database, wherein a device entry in the database for the medical device includes at least one component entry for a recyclable component in the medical device;

tracking a usage of the medical device by a patient;
updating a remaining life of the recyclable component based on the usage of the medical device;
upon determining the patient is finished with the medical device, determining whether the recyclable component has sufficient remaining life to be recycled based on a threshold;
upon determining the recyclable component has sufficient remaining life, outputting instructions to remove the recyclable component from the medical device; and
outputting instructions to transport the recyclable component to be placed in a new medical device; and
predicting a number of medical devices that will be available for recycling at a future date using a machine learning (ML) model, wherein the ML model comprises at least one of a neural network, and is trained by:
tracking an amount of time each of a first plurality of patients used a first plurality of medical devices;
receiving medical information, including at least a diagnosis, for each of the first plurality of patients; and
using the amount of time and the medical information to correlate the amount of time and the medical information.

10. The non-transitory computer readable medium of claim 9, wherein the device entry for the medical device comprises a second component entry for a second recyclable component in the medical device, the operation further comprising:
upon determining the patient is finished with the medical device, determining that the second recyclable component does not have sufficient remaining life to be recycled based on the threshold, wherein the second recyclable component is discarded.

11. The non-transitory computer readable medium of claim 9, the operation further comprising:
registering the new medical device built using the recyclable component in the database, wherein a device entry in the database for the new medical device includes at least one component entry for the recyclable component indicating the recyclable component has an component lifetime that matches the remaining life of the recyclable component when the patient was finished with the medical device.

12. The non-transitory computer readable medium of claim 9, wherein the at least one component entry for the recyclable component stores a component lifetime indicating an expected lifetime of the recyclable component, a component usage time of the recyclable component, the remaining life of the recyclable component, and an indicator indicating whether the recyclable component should undergo a sterilization process before being recycled into the new medical device.

13. The non-transitory computer readable medium of claim 12, the operation further comprising, before determining whether the recyclable component has sufficient remaining life to be recycled:
adjusting the remaining life of the recyclable component based on the sterilization process.

14. The non-transitory computer readable medium of claim 9, to predict the number of medical devices that will be available for recycling at the future date using the machine learning (ML) model, the operation comprising:
inputting medical information, including at least a diagnosis, for a second plurality of patients that are currently assigned to use a second plurality of medical devices; and receiving indications from the ML model predicting which of the second plurality of medical devices will be available for recycling by the future date.

15. A system, comprising:
a processor; and
memory storing code which, when executed by the processor, performs an operation, the operation comprising:
registering a one-time use medical device in a database, wherein a device entry in the database for the medical device includes at least one component entry for a recyclable component in the medical device;
tracking a usage of the medical device by a patient;
updating a remaining life of the recyclable component based on the usage of the medical device;
upon determining the patient is finished with the medical device, determining whether the recyclable component has sufficient remaining life to be recycled based on a threshold;
upon determining the recyclable component has sufficient remaining life, outputting instructions to remove the recyclable component from the medical device; and
outputting instructions to transport the recyclable component to be placed in a new medical device; and
predicting a number of medical devices that will be available for recycling at a future date using a machine learning (ML) model, wherein the ML model comprises at least one of a neural network, and is trained by:
tracking an amount of time each of a first plurality of patients used a first plurality of medical devices;
receiving medical information, including at least a diagnosis, for each of the first plurality of patients; and
using the amount of time and the medical information to correlate the amount of time and the medical information.

16. The system of claim 15, the operation further comprising:
determining a number of recycled components from the number of medical devices predicted by the ML model;
determining a number of new components available for assembling with the number of recycled components to produce a first plurality of new medical devices;
estimating a number of the first plurality of new medical devices based on the number of recycled components and the number of new components; and
ordering a second plurality of new medical devices to satisfy an overall demand for new medical devices along with the first plurality of new medical devices built from recycled components.

17. The system of claim 15, wherein the operation further comprises:
registering the new medical device built using the recyclable component in the database, wherein a device entry in the database for the new medical device includes at least one component entry for the recyclable component indicating the recyclable component has an component lifetime that matches the remaining life of the recyclable component when the patient was finished with the medical device.

18. The system of claim 15, wherein the at least one component entry for the recyclable component stores a component lifetime indicating an expected lifetime of the recyclable component, a component usage time of the recyclable component, the remaining life of the recyclable component, and an indicator indicating whether the recyclable component should undergo a sterilization process before being recycled into the new medical device,
   wherein the operation further comprises, before determining whether the recyclable component has sufficient remaining life to be recycled:
      adjusting the remaining life of the recyclable component based on the sterilization process.

19. The system of claim 15, to predict the number of medical devices that will be available for recycling at the future date using the machine learning (ML) model, the operation comprising:
   inputting medical information, including at least a diagnosis, for a second plurality of patients that are currently assigned to use a second plurality of medical devices; and
   receiving indications from the ML model predicting which of the second plurality of medical devices will be available for recycling by the future date.

20. The non-transitory computer readable medium of claim 9, the operation further comprising:
   determining a number of recycled components from the number of medical devices predicted by the ML model;
   determining a number of new components available for assembling with the number of recycled components to produce a first plurality of new medical devices;
   estimating a number of the first plurality of new medical devices based on the number of recycled components and the number of new components; and
   ordering a second plurality of new medical devices to satisfy an overall demand for new medical devices along with the first plurality of new medical devices built from recycled components.

* * * * *